(12) United States Patent
Khachi

(10) Patent No.: US 8,038,598 B2
(45) Date of Patent: Oct. 18, 2011

(54) BALLOON ENDOSCOPE DEVICE

(75) Inventor: Gerald J. Khachi, Augusta, GA (US)

(73) Assignee: Baystate Health, Inc., Springfield, MA (US)

( * ) Notice: Subject to any disclaimer, the term of this patent is extended or adjusted under 35 U.S.C. 154(b) by 781 days.

(21) Appl. No.: 11/747,693

(22) Filed: May 11, 2007

(65) Prior Publication Data

US 2008/0009673 A1    Jan. 10, 2008

Related U.S. Application Data

(60) Provisional application No. 60/800,374, filed on May 15, 2006.

(51) Int. Cl.
*A61B 1/00* (2006.01)
*A61M 29/00* (2006.01)

(52) U.S. Cl. ............ 600/116; 600/115; 604/101.01

(58) Field of Classification Search .......... 600/115, 600/116, 153, 121, 154; 604/101.01, 95.03, 604/97.01, 101.05, 103.02
See application file for complete search history.

(56) References Cited

U.S. PATENT DOCUMENTS

| | | | | |
|---|---|---|---|---|
| 3,913,565 A | | 10/1975 | Kawahara | |
| 3,915,157 A | | 10/1975 | Mitsui | |
| 4,040,413 A | * | 8/1977 | Ohshiro | 600/116 |
| 4,141,364 A | * | 2/1979 | Schultze | 128/207.15 |
| 4,146,019 A | | 3/1979 | Bass et al. | |
| 4,148,307 A | * | 4/1979 | Utsugi | 600/116 |
| 4,406,656 A | * | 9/1983 | Hattler et al. | 604/523 |
| 4,470,407 A | | 9/1984 | Hussein | |
| 4,616,631 A | * | 10/1986 | Takahashi | 600/139 |
| 4,750,477 A | | 6/1988 | Wardle | |
| 4,976,710 A | | 12/1990 | Mackin | |
| 5,025,778 A | | 6/1991 | Silverstein et al. | |
| 5,308,323 A | * | 5/1994 | Sogawa et al. | 604/95.03 |
| 5,353,783 A | * | 10/1994 | Nakao et al. | 600/106 |
| 5,441,485 A | * | 8/1995 | Peters | 604/101.01 |
| 5,501,667 A | | 3/1996 | Verduin, Jr. | |
| 5,503,616 A | | 4/1996 | Jones | |
| 5,607,441 A | | 3/1997 | Sierocuk et al. | |
| 5,658,311 A | * | 8/1997 | Baden | 606/192 |
| 5,707,382 A | | 1/1998 | Sierocuk et al. | |
| 5,762,604 A | | 6/1998 | Kieturakis | |
| 5,891,013 A | | 4/1999 | Thompson | |
| 5,938,585 A | | 8/1999 | Donofrio | |
| 6,086,528 A | | 7/2000 | Adair | |
| 6,211,904 B1 | | 4/2001 | Adair et al. | |
| 6,234,958 B1 | * | 5/2001 | Snoke et al. | 600/114 |
| 6,277,065 B1 | | 8/2001 | Donofrio | |

(Continued)

FOREIGN PATENT DOCUMENTS

WO    WO 90/14859    12/1990

*Primary Examiner* — Linda Dvorak
*Assistant Examiner* — Alireza Nia
(74) *Attorney, Agent, or Firm* — Holland & Bonzagni, P.C.; Mary R. Bonzagni, Esq.

(57) ABSTRACT

A balloon endoscope device having a shaft with a distal end that allows for blunt dissection is provided. The shaft utilizes a plurality of separately inflatable balloons that alone or together with exterior functional channels (e.g., instrument channels, air channels, water channels, suction channels) circumferentially surround the distal end of the shaft to better position and maneuver the distal end as it advances through tissue planes and once it reaches a target working space or operative site.

18 Claims, 1 Drawing Sheet

U.S. PATENT DOCUMENTS

| | | |
|---|---|---|
| 6,352,503 B1 | 3/2002 | Matsui et al. |
| 6,527,753 B2 | 3/2003 | Sekine et al. |
| 6,577,891 B1 * | 6/2003 | Jaross et al. .................. 600/473 |
| 6,899,674 B2 | 5/2005 | Viebach et al. |
| 6,921,364 B2 | 7/2005 | Mollenauer et al. |
| 6,988,986 B2 | 1/2006 | Gross |
| 6,989,018 B2 | 1/2006 | Fogarty et al. |
| 7,001,404 B1 | 2/2006 | Chin |
| 7,001,405 B2 | 2/2006 | Kieturakis et al. |
| 7,022,068 B2 | 4/2006 | Kim et al. |
| 7,963,911 B2 * | 6/2011 | Turliuc ........................ 600/115 |
| 2004/0147807 A1 | 7/2004 | Viebach et al. |
| 2004/0158125 A1 | 8/2004 | Aznoian et al. |
| 2005/0054900 A1 | 3/2005 | Mawn et al. |
| 2005/0065504 A1 | 3/2005 | Melsky et al. |
| 2005/0124856 A1 | 6/2005 | Fujikura et al. |
| 2005/0159645 A1 | 7/2005 | Bertolero et al. |
| 2005/0197531 A1 | 9/2005 | Cabiri et al. |
| 2006/0047184 A1 | 3/2006 | Banik et al. |

* cited by examiner

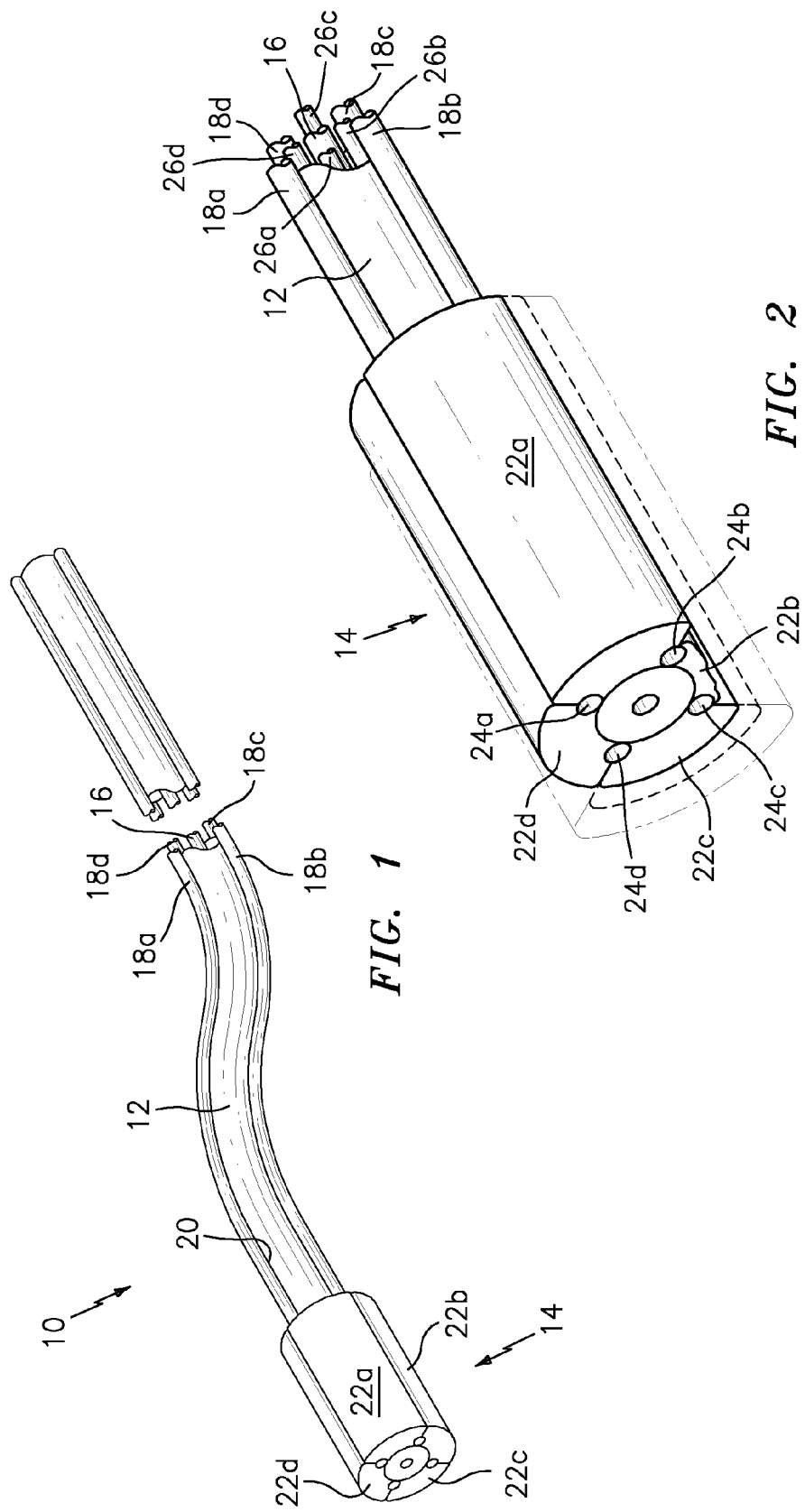

BALLOON ENDOSCOPE DEVICE

RELATED APPLICATION

This application claims the benefit of U.S. Provisional Patent Application Ser. No. 60/800,374, filed May 15, 2006, which is fully incorporated herein by reference.

TECHNICAL FIELD

The present invention generally relates to an endoscope device having a shaft with a distal end that allows for blunt dissection, and more particularly relates to an endoscope device that utilizes a plurality of inflatable balloons circumferentially surrounding the distal end of the device's shaft to better position and maneuver the distal end as it advances through tissue planes and once it reaches a target working space or operative site.

BACKGROUND AND SUMMARY OF THE INVENTION

Endoscopes have been used for many years for viewing within a desired region of a patient's body through the patient's airway, other natural orifices, or a surgical incision. An endoscope typically has an elongated flexible shaft with a control head at its proximal end. The flexible shaft is equipped with one or more functional channels (e.g., instrument channels, air channels, irrigation channels, suction channels) that extend along the length of the flexible shaft from the distal end to the control head. The control head is connected to a light source, air/water supply and suction via an "umbilical" cord.

For fiber-optic endoscopes, the flexible shaft is also equipped with a channel holding optical fibers (i.e., an image guide) for carrying an image from the distal end of the shaft to the control head, where it can be viewed through an eyepiece by a physician.

For video-endoscopes, a Charge Coupled Device (CCD), which serves as an image-capturing means, is located at the distal end of the endoscope. Captured images are compressed and recorded on, for example, a hard disk, a removable memory device, an optical disk, or a magneto-optical (MO) disk.

The tip of the endoscope is controlled using pull wires attached at the tip just beneath the surface of the flexible shaft, and passing back through the length of the shaft to angling controls in the control head of the endoscope. Two angling wheels or knobs located on the control head for up/down and right/left movement incorporate a friction braking system, so that the tip can be fixed temporarily in any desired position.

Surgeons in the past have used blunt-tipped instruments as well as balloons in connection with endoscopic surgery to dissect tissue in order to develop a working space in the interior of the body. Balloon type surgical instruments have been developed to assist in this regard. Several of these prior art instruments are described below.

U.S. Pat. No. 5,762,604 describes a surgical instrument that utilizes an inflatable, transparent balloon. The instrument serves to dissect and form a dissected viewing space within the interior of the body to provide adequate depth of field for endoscopic viewing. The instrument includes a transparent tipped dissector-guide 5 having a guide member 10 with an interior lumen (cavity) 14 (dimensioned to accommodate a viewing scope or endoscope 22) as well as a working channel 34 (for an elongate trocar). The guide member 10 affords the surgeon contemporaneous vision through the far end of the guide 10 as the instrument navigates the interior of the body. Metal band 132 and balloon constraining sleeve 133 are employed to constrain balloon 120 in a first collapsed position around guide member 10. The constraining sleeve 133 is provided with a weakened, perforated surface that will give way and burst when an inflation medium is introduced into balloon chamber 122 allowing the balloon to deploy to the inflated position. As the balloon inflates, tissue is dissected by the balloon generally applying forces perpendicular to the tissue being dissected or separated. When balloon 120 is inflated, it is disposed in a "hot dog bun" shape around the guide 10, offering increased depth of field in all directions around lens 32 of endoscope 22. Procedures are described in this patent as being performed on an outer surface of the inflated balloon. See e.g., Cols. 7 to 8, lines 60 to 3, of the '604 patent.

U.S. Pat. Nos. 5,607,441 and 5,707,382 both describe a surgical instrument that includes an assembly 10 consisting of two primary components, namely, a balloon dissector 11 for the dissection of internal bodily tissue to form an operative space during a surgical procedure, and an endoscope 12 for providing simultaneous visualization during the surgical procedure as the dissector is advanced through tissue and the operative space is formed. The balloon dissector 11 basically comprises a conventional trocar cannula 13, an extension assembly 14 (with transparent tissue-contacting element 24), and an inflatable balloon 15. Tubular sleeve 17 connects trocar cannula 13 and extension assembly 14 and is sized to receive an endoscope. An endoscope would be inserted distally in assembly 10 through tubular sleeve 17 until it abuts ring 23 at the distal end of the extension assembly 14. Use of assembly 10 is described in Cols. 5 to 6, lines 55 to 19, of the '382 patent, and is shown in FIGS. 3 to 5, of this patent. To summarize, once the assembly 10 is positioned parallel to adjacent tissue layers with the aid of the endoscope, the balloon 15 is inflated to form an operative space. The balloon 15 is then deflated, and the assembly including the balloon dissector 11 removed and another trocar cannula 35 introduced into the operative space.

U.S. Pat. Nos. 5,938,585 and 6,277,065 both describe an anchoring and positioning balloon device shaped like a cradle that is deployed using a side-view type endoscope 10. Endoscope 10 includes an illumination device 20, a viewing device 22, and a working lumen or channel 24, all contained within window section 18. A cradle shaped inflatable balloon 30 is attached to the distal end section 12 of the endoscope 10. During operation of the endoscope 10 with the balloon 30 inflated, the cradle portion 34 spaces the window section 18 from the examining area, thus providing a good view of and a sufficient working space relative to the body cavity wall 27 (see Cols. 3 to 4, lines 59 to 7, of the '065 patent).

US 2005/0159645 A1 describes a sheath for use with a medical device such as an endoscope, that comprises: an elongated body having a proximal end and a distal end; a main lumen extending through the elongated body from the proximal end to the distal end; and one or more inflatable balloons mounted on an outside surface of the elongated body proximate to the distal end. Embodiments employing multiple balloons mount the balloons 16, 18, 52, 54, 56 in isolated fashion on the distal end of the elongated body (see FIGS. 1A, 1B, 1C), or along the length of the elongated body (see FIGS. 4A and 4B).

Unfortunately, the use of single balloons or multiple isolated balloons on the distal end of these prior art devices renders the positioning and advancement of the devices between/through natural tissue planes difficult to control.

It is therefore an object of the present invention to provide an endoscope device capable of blunt dissection that allows for improved control over the positioning of the distal end of the device's shaft between natural tissue planes (e.g., subcutaneous, subfascial, intraperitoneal, intrathoracic, intracranial tissue planes) and further allows for improved control over the shaft's advancement through these tissue planes.

The present invention therefore provides an endoscope device that comprises a shaft having a distal end and a plurality of separately inflatable balloons that alone or together with exterior functional channels (e.g., instrument channels, air channels, water channels, suction channels) circumferentially surround the distal end of the shaft.

In a preferred embodiment, the inventive endoscope device comprises: a shaft made up of a flexible or partially flexible tubular member having a distal end, and interior optical and inflation channels extending there through; functional channels adapted to extend along an outer surface of the tubular member; and a plurality of separately inflatable balloons, where the balloons together with the exterior functional channels circumferentially surround the distal end of the tubular member.

The present invention further provides a method of dissecting layers of tissue to form a working space between the tissue layers and then performing an endoscopic procedure within the newly formed working space, which method comprises:
  providing an endoscope device as described hereinabove, wherein the balloons located on the distal end of the device's shaft are fully deflated;
  inserting the distal end of the shaft between the layers of tissue;
  advancing the distal end of the shaft between the tissue layers by sequentially inflating and deflating various balloons until a desired length of dissection has been completed;
  inflating all or some of the balloons to form a working space between the tissue layers; and
  repositioning the distal end of the shaft within the newly formed working space, as necessary, while performing an endoscopic procedure therein by inflating and deflating various balloons.

Other features and advantages of the invention will be apparent to one of ordinary skill from the following detailed description and accompanying drawings. Unless otherwise defined, all technical and scientific terms used herein have the same meaning as commonly understood by one of ordinary skill in the art to which this invention belongs. All publications, patent applications, patents and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

Particular features of the disclosed invention are illustrated by reference to the accompanying drawings, in which:

FIG. 1 is a perspective side view of a preferred embodiment of the shaft of the endoscope device of the present invention; and FIG. 2 is an enlarged perspective view of the distal end of the shaft shown in FIG. 1.

DETAILED DESCRIPTION OF THE PREFERRED EMBODIMENT

Although the shaft as described herein forms part of an endoscope device, it is not so limited. The inventive shaft may be used as a shaft for a catheter or other similar device, or it may constitute a jacket or sheath for such a medical or surgical device for adding protection and functionality thereto.

Moreover, although the ability of the inventive endoscope device to more effectively and efficiently perform blunt dissection of tissue planes will be emphasized herein, the device's balloons may be used for a number of other purposes, including, but not limited to, distending a body cavity (e.g., peritoneal cavity) in which an operation is to take place, thereby obviating the need for insufflation, facilitating intubation of, for example, the ampula of vater by acting as a scaffold against the duodenum wall, and blocking blood vessels to control bleeding/hemorrhaging. Moreover, and as will be readily appreciated by one skilled in the art, the device's balloons serve as a cushion to protect the mucosa during endoscopic procedures requiring the device's shaft to follow a tortuous path (e.g., endoscopic colon and rectal procedures), thereby decreasing iatrogenic injuries.

Referring now to the drawings in detail, a preferred embodiment of the shaft of the balloon endoscope device of the present invention is shown generally at 10. Shaft 10 is part of an end-view type endoscope device that allows for blunt dissection of tissue planes, while providing an operator with an image (e.g., a charge-coupled image). As best shown in FIG. 1, shaft 10 basically comprises: (a) a flexible or partially flexible tubular member 12 having a distal end 14, and an interior optical channel 16 and four interior inflation channels 26a, 26b, 26c, 26d (shown in FIG. 2) extending there through; (b) four functional channels 18a, 18b, 18c, 18d, adapted to extend along an outer surface 20 of the tubular member 12; and (c) four separately inflatable balloons 22a, 22b, 22c, 22d. In this embodiment, each interior inflation channel is in fluid communication with a different balloon or balloon chamber, and all such inflation channels are in further fluid communication with a control means, such as a handheld control dial, for separately inflating and deflating each balloon 22a, 22b, 22c, 22d.

As best shown in FIG. 2, functional channels 18a, 18b, 18c, 18d, terminate in exit ports 24a, 24b, 24c, 24d, and together with balloons 22a, 22b, 22c, 22d, circumferentially surround the distal end 14 of the tubular member 12. Balloons 22a, 22b, 22c, 22d, in both an inflated and deflated state, wrap around exit ports 24a, 24b, 24c, 24d. A plurality of working sizes for balloon 22c are shown in FIG. 2, two of these working sizes being shown in phantom. Opposing channels 18b and 18d are used to supply either irrigation fluid or suction, while opposing channels 18a and 18c are instrument channels, which may be used to deliver any surgical instrument adapted to contact, grasp or sever tissue including, but not limited to, forceps, scissors, knives, staplers, clip appliers, and other like devices. Although these channels are shown as circular in cross-section, their cross-section could be trapezoidal or any other suitable shape.

When balloons 22a, 22b, 22c, 22d, are fully deflated, their thickness approximates the outside diameter of the functional channels 18a, 18b, 18c, 18d, thereby forming a substantially uniform layer in terms of thickness about the distal end 14 of the tubular member 12. It is noted that the use of a plurality of smaller-sized balloons on the distal end 14 of the shaft 10 eliminates the need to physically constrain these balloons during introduction of the shaft 10 into a body cavity. When balloons 22a, 22b, 22c, 22d, are all at least partially inflated, the balloons touch adjacent balloons and form a substantially continuous outer surface about the distal end 14 of the tubular member 12.

As will be readily evident to one skilled in the art, in addition to allowing for improved control over its positioning and advancement through tissue planes, which will be described in more detail below, the inventive balloon endoscope device provides an operator with images (e.g., charge-coupled or video images) of the area being dissected as well as the ability to, among other things, apply clips, irrigate, apply suction and cut vessels as the shaft 10 is being advanced. Once a desired length of dissection has been completed, all or some of the balloons may be inflated to form a working space between the tissue layers, at which time necessary surgical instruments may be introduced through functional channels 18a, 18c, to perform the desired procedure(s).

The balloon endoscope shaft 10 of the present invention can be sized to render it suitable for performing a number of different medical or surgical procedures. By way of example, the inventive shaft 10 may be used for (1) plastic surgical procedures (e.g., cosmetic procedures such as brow lifts and facelifts), allowing subcutaneous tissue and fascial planes to be pulled up or elevated with only a very small incision, resulting in a beneficial decrease in the amount of scarring, (2) intracranial procedures such as evaluating and/or evacuating a hematoma using small bur holes in the skull, (3) harvesting veins without the need for long incisions that are susceptible to wound break down and infection, (4) general surgical procedures (e.g., endoscopic and laparoscopic gastrointestinal procedures including endoscopic colonoscopies), (5) thoracic surgical procedures, eliminating the need for single lung ventilation anesthesia (i.e., deflating and stopping ventilation to the lung involved in a procedure) and thereby allowing a patient, who typically has low pulmonary reserve and would not tolerate single lung ventilation, to continue to breathe from both lungs, and (6) bariatric surgical procedures. Preferred outside diameters for the inventive shaft 10 when used for the above-described medical or surgical procedures are set forth in Table 1 below.

TABLE 1

| Medical or Surgical Procedure | O.D.$_{min}$[1] (mm) | O.D.$_{max}$[2] (mm) |
|---|---|---|
| Plastic surgical procedures | 3-5 | 15-20 |
| Intracranial procedures | 3-5 | 10-15 |
| Vein harvesting | 5-8 | 25-30 |
| General surgical procedures | 5-20 | 25->150 |
| Thoracic surgical procedures | 5-20 | 25-150 |
| Bariatric surgical procedures | 5-8 | 25-30 |

[1]O.D.$_{min}$ - The outside diameter in millimeters (mm) when the balloons are fully deflated.
[2]O.D.$_{max}$ - The outside diameter in mm when the balloons are fully inflated.

In addition to the benefits noted above, the inventive balloon endoscope device obviates the need for insufflation and thus the need for administering anesthesia or paralyzing agents to a patient, thereby allowing certain laparoscopic procedures, while still performed in an operating room, to be carried out more cost effectively and with reduced risk to the patient. The inventive endoscope device allows other laparoscopic procedures such as laparoscopic exploration and tissue biopsy of the peritoneal and retroperitoneal spaces to be performed bedside for critically ill and unstable patients.

The balloons used in the present invention may adopt any size and shape, but preferably are sized and shaped so as to collectively form a substantially continuous surface about the distal end 14 of the tubular member 12 when all are similarly inflated. In a preferred embodiment, and as best shown in FIG. 2, each balloon 22a, 22b, 22c, 22d, has a trapezoidal cross-sectional shape. Each balloon may have one or more internal chambers and each has the ability to be expanded to a plurality of working sizes upon the application of given pressures through its respective inflation channel without bursting.

Balloons suitable for use in the present invention may be made using compliant materials, non-compliant materials, or a combination of complaint and non-compliant materials. As is well known to those skilled in the art, balloons made solely from compliant materials (e.g., polyethylene, polyolefin, polyurethane) expand and stretch with increasing pressure within the balloon, while balloons made solely from non-compliant materials remain at a pre-selected diameter as the internal balloon pressure increases beyond that required to fully inflate the balloon.

As will be readily evident to those skilled in the art, by inflating and deflating the various balloons 22a, 22b, 22c, 22d, the distal end 14 of the tubular member 12 of the endoscope shaft 10 can be moved either left or right, up or down, clockwise or counter-clockwise, thereby providing the operator with the ability to finely adjust the position of the distal end 14 of the tubular member 12 beyond that which is achievable by the angling controls in the control head of the endoscope.

The construction of the remaining parts or components of the endoscope shaft 10 (i.e., tubular member 12, interior optical channel 16, interior inflation channels 26a, 26b, 26c, 26d, functional channels 18a, 18b, 18c, 18d, inflation/deflation control means), as well as, other parts or components of the endoscope (e.g., the control head, the light source(s), image guides or image-capturing/compressing/recording means, air/water/suction supply, etc.) are well-known in the art and do not form a part of this invention.

While various embodiments of the present invention have been described above, it should be understood that they have been presented by way of example only, and not limitation. Thus, the breadth and scope of the present invention should not be limited by any of the exemplary embodiments.

Having thus described the invention, what is claimed is:

1. An endoscope device, which comprises: a shaft having a distal end, and interior optical and inflation channels extending there through; a plurality of exterior functional channels adapted to extend along an outer surface of the shaft, the plurality of exterior functional channels terminating in a plurality of exit ports at the distal end of the shaft; and a plurality of separately inflatable balloons that in both an inflated and deflated state wrap around the plurality of exit ports which are located between the separately inflatable balloons, wherein the balloons touch adjacent balloons and form a substantially continuous outer surface about the distal end of the shaft in both an inflated and deflated state.

2. The endoscope device of claim 1, wherein when the balloons are inflated, they form a substantially continuous outer surface about the distal end of the shaft.

3. The endoscope device of claim 2, wherein each balloon has a trapezoidal cross-sectional shape.

4. The endoscope device of claim 1, wherein the shaft has a minimum outer diameter ranging from about 3 to about 5 millimeters, and a maximum outer diameter ranging from about 15 to about 20 millimeters, thereby rendering the endoscope device suitable for plastic surgical procedures.

5. The endoscope device of claim 1, wherein the shaft has a minimum outer diameter ranging from about 3 to about 5 millimeters, and a maximum outer diameter ranging from about 10 to about 15 millimeters, thereby rendering the endoscope device suitable for intracranial procedures.

6. The endoscope device of claim 1, wherein the shaft has a minimum outer diameter ranging from about 5 to about 8 millimeters, and a maximum outer diameter ranging from about 25 to about 30 millimeters, thereby rendering the endoscope device suitable for vein harvesting and bariatric surgical procedures.

7. The endoscope device of claim 1, wherein the shaft has a minimum outer diameter ranging from about 5 to about 20 millimeters, and a maximum outer diameter ranging from about 25 to greater than about 150 millimeters, thereby rendering it suitable for general and thoracic surgical procedures.

8. The endoscope device of claim 1, wherein the exterior functional channels are adapted to supply irrigation fluid, suction, or surgical instruments.

9. An endoscope device, which comprises:
  (a) a shaft comprising a flexible or partially flexible tubular member having a distal end, and interior optical and inflation channels extending there through;
  (b) a plurality of exterior functional channels adapted to extend along an outer surface of the tubular member, the plurality of exterior functional channels terminating in a plurality of exit ports at the distal end of the tubular member, wherein each functional channel has a similar outside diameter; and
  (c) a plurality of similarly sized separately inflatable balloons that in both an inflated and deflated state wrap around the plurality of exit ports which are located between the separately inflatable balloons, wherein the balloons touch adjacent balloons and form a substantially continuous outer surface about the distal end of the tubular member in both an inflated and deflated state.

10. The endoscope device of claim 9, wherein when the balloons are deflated, their thickness approximates the outside diameters of the functional channels, thereby forming a substantially uniform layer in terms of thickness about the distal end of the tubular member.

11. The endoscope device of claim 10, wherein when the balloons are inflated, they form a substantially continuous outer surface about the distal end of the tubular member.

12. The endoscope device of claim 9, wherein the balloons are made using compliant materials, non-compliant materials, or a combination of compliant and non-compliant materials.

13. The endoscope device of claim 9, wherein the exterior functional channels are adapted to supply irrigation fluid, suction, or surgical instruments.

14. An endoscope device, wherein the endoscope device is an end-view type endoscope device, which comprises:
  (a) a shaft comprising a flexible or partially flexible tubular member having a distal end, and an interior optical channel and a plurality of interior inflation channels extending there through;
  (b) a plurality of exterior functional channels adapted to extend along an outer surface of the tubular member, the plurality of exterior functional channels terminating in a plurality of exit ports at the distal end of the tubular member, wherein each functional channel has a similar outside diameter;
  (c) a plurality of similarly sized separately inflatable balloons that in both an inflated and deflated state wrap around the plurality of exit ports which are located between the separately inflatable balloons, wherein the balloons touch adjacent balloons and form a substantially continuous outer surface about the distal end of the tubular member in both an inflated and deflated state; and
  (d) control means for separately inflating and deflating each balloon, wherein, each interior inflation channel is in fluid communication with a different balloon, and all such inflation channels are in further fluid communication with the control means.

15. The endoscope device of claim 14, wherein the exterior functional channels are adapted to supply irrigation fluid, suction, or surgical instruments.

16. An endoscope device, wherein the endoscope device is an end-view type endoscope device, which comprises:
  (a) a shaft comprising a flexible or partially flexible tubular member having a distal end, and an interior optical channel and four interior inflation channels extending there through;
  (b) four exterior functional channels adapted to extend along an outer surface of the tubular member, the four exterior functional channels terminating in four exit ports at the distal end of the tubular member, wherein each functional channel has a similar outside diameter;
  (c) four similarly sized separately inflatable balloons that in both an inflated and deflated state wrap around the four exit ports which are located between the separately inflatable balloons, wherein the balloons touch adjacent balloons and form a substantially continuous outer surface about the distal end of the tubular member in both an inflated and deflated state; and
  (d) control means for separately inflating and deflating each balloon, wherein, each interior inflation channel is in fluid communication with a different balloon, and all such inflation channels are in further fluid communication with the control means.

17. The endoscope device of claim 16, wherein when the balloons are inflated, they form a substantially continuous outer surface about the distal end of the tubular member.

18. The endoscope device of claim 16, wherein the exterior functional channels are adapted to supply irrigation fluid, suction, or surgical instruments.

* * * * *